US009332907B2

(12) United States Patent
Vija (10) Patent No.: US 9,332,907 B2
(45) Date of Patent: May 10, 2016

(54) EXTRACTING APPLICATION DEPENDENT EXTRA MODAL INFORMATION FROM AN ANATOMICAL IMAGING MODALITY FOR USE IN RECONSTRUCTION OF FUNCTIONAL IMAGING DATA

(71) Applicant: Alexander Hans Vija, Evanston, IL (US)

(72) Inventor: Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 498 days.

(21) Appl. No.: 13/852,029

(22) Filed: Mar. 28, 2013

(65) Prior Publication Data

US 2013/0267841 A1  Oct. 10, 2013

Related U.S. Application Data

(63) Continuation-in-part of application No. 12/369,159, filed on Feb. 11, 2009, now Pat. No. 8,577,103.

(60) Provisional application No. 61/737,197, filed on Dec. 14, 2012.

(51) Int. Cl.
| | | |
|---|---|---|
| G06K 9/00 | (2006.01) | |
| A61B 5/00 | (2006.01) | |
| G06T 11/00 | (2006.01) | |
| G06T 7/00 | (2006.01) | |

(52) U.S. Cl.
CPC ............. *A61B 5/0035* (2013.01); *G06T 7/0081* (2013.01); *G06T 11/005* (2013.01); *G06T 2207/10081* (2013.01); *G06T 2207/30008* (2013.01); *G06T 2207/30056* (2013.01); *G06T 2207/30061* (2013.01)

(58) Field of Classification Search
USPC ................................................. 382/128–132
See application file for complete search history.

(56) References Cited

U.S. PATENT DOCUMENTS

| | | | | |
|---|---|---|---|---|
| 4,339,799 | A * | 7/1982 | Abele ..................... | A61B 6/032 378/11 |
| 4,792,900 | A * | 12/1988 | Sones .................. | A61B 6/4241 378/98.9 |
| 6,205,348 | B1 * | 3/2001 | Giger ..................... | A61B 6/482 382/128 |
| 6,950,494 | B2 | 9/2005 | Vija et al. | |
| 7,263,214 | B2 * | 8/2007 | Uppaluri ................ | G06T 7/0012 382/128 |
| 7,272,429 | B2 * | 9/2007 | Walker ..................... | A61B 6/032 378/4 |
| 7,378,660 | B2 * | 5/2008 | Case ...................... | G01T 1/1611 250/363.01 |
| 7,379,575 | B2 * | 5/2008 | Ruhrnschopf ............ | G06T 5/50 128/922 |
| 2005/0135664 | A1 * | 6/2005 | Kaufhold .............. | G06T 11/006 382/131 |
| 2005/0259857 | A1 * | 11/2005 | Jeunehomme ........ | G06T 7/0012 382/132 |
| 2009/0087065 | A1 * | 4/2009 | DaSilva ................ | A61B 6/037 382/131 |
| 2010/0014730 | A1 | 1/2010 | Hahn et al. | |
| 2010/0104151 | A1 * | 4/2010 | Bertens ................. | G06T 7/0012 382/128 |
| 2012/0063662 | A1 * | 3/2012 | Kwon ..................... | G06T 5/003 382/132 |
| 2013/0077844 | A1 * | 3/2013 | Vija ...................... | G06T 7/0012 382/131 |
| 2014/0079304 | A1 * | 3/2014 | Foo ....................... | G06T 7/0081 382/131 |

* cited by examiner

*Primary Examiner* — Wesley Tucker
(74) *Attorney, Agent, or Firm* — Peter Kendall (57) ABSTRACT

Segmentation is provided in multi-modal reconstruction of functional information. Rather than using HU values for segmentation, the HU values are converted into linear attenuation coefficients, such as in a μ-map (Mu map). The conversion uses different functions for different ranges of the HU values. Linear attenuation coefficients are less likely subject to variation by patient, protocol, or scanner. The resulting segmentation may be more consistent across various clinical settings, providing for more accurate multi-modal reconstruction.

20 Claims, 6 Drawing Sheets

| #ZONES | HV | | 3/1/2012 | LAC SOURCE: | HTTP://WWW.PHYSICS.NIST.GOV/PHYSREFDATA/XCOM/HTML/XCOM1.HTML | | | | |
|---|---|---|---|---|---|---|---|---|---|---|
| | 1 | 3 | 5 | | | | 7 | | 12% | -12% |
| | | | | | | TOTAL LAC W/ COHERENT SCATTER (1/CM) | | | MAX | MIN |
| | | | | MATERIAL | LAC (140keV) | RATIO TO CB | | CENTER | | |
| INSIDE | BONE | CBONE | CB | 0.278919 | 1 | CB | 0.278919 | 0.312389 | 0.274903 |
| | | | CB2-50% | 0.236512 | 0.847959443 | CB2-50% | 0.236512 | 0.264853 | 0.223106 |
| | | | CB2-30% | 0.202616 | 0.726433122 | CB2-30% | 0.202616 | 0.22693 | 0.198698 |
| | | SB | B-200 BONE MINERAL | 0.174103 | 0.624206311 | SOFT BONE | 0.62177 | 0.696383 | 0.612617 |
| | | | IB-INNER BONE (RMI 456) | 0.172744 | 0.619333928 | | | | |
| | T | | LV1 LIVER | 0.164496 | 0.589762619 | SOFT TISSUE | 0.567763 | 0.635854 | 0.509587 |
| | | ST | SOFT TISSUE (ICRU-44) | 0.16112 | 0.577658747 | | | | |
| | | | LUNG (ICRU-44) | 0.16065 | 0.575973367 | | | | |
| | | | WATER, LIQUID | 0.154 | 0.552131622 | | | | |
| | | | SOLID WATER RMI 457 | 0.151533 | 0.543286761 | | | | |
| | AD | | ADIPOSE, AP6, RMI453 | 0.14715 | 0.527572521 | ADIPOSE, AP6, RMI453 | 0.527573 | 0.580881 | 0.319975 |
| LUNG AND LESS LUNG | LUNG AND LESS LUNG | | LUNG, LN450 | 0.066 | 0.236627838 | LUNG | 0.198916 | 0.213826 | 0.188166 |
| | | | LUNG (LN300) RMI455 | 0.0405 | 0.145243446 | | | | |
| | | | AIR | | | | | | |

EXTRACTING APPLICATION DEPENDENT EXTRA MODAL INFORMATION FROM AN ANATOMICAL IMAGING MODALITY FOR USE IN RECONSTRUCTION OF FUNCTIONAL IMAGING DATA

CROSS-REFERENCE TO RELATED APPLICATION

This application is a continuation-in-part of U.S. patent application Ser. No. 12/369,159, filed Feb. 11, 2009, and claims the benefit of priority under 35 U.S.C. §119(e) of U.S. Provisional Patent Application No. 61/737,197, filed on Dec. 14, 2012, the disclosures of which are incorporated herein by reference.

BACKGROUND

The present embodiments relate to functional imaging. In particular, segmentation for multi-modal functional imaging is provided.

Medical imaging of metabolic and biochemical activity within a patient is known as functional imaging. Functional imaging techniques include, for example, nuclear imaging such as Positron Emission Tomography (PET), Single Photon Computed Tomography (SPECT), functional magnetic resonance imaging (fMRI), and functional computed tomography (fCT). The reconstruction of a functional image from data acquired by functional imaging is often difficult because the data is characterized by small signal rates and low signal-to-noise ratio. For nuclear imaging, for example, the count rate is limited by the amount of a radioactive substance that can be administered without harming the patient. Nuclear imaging relies on emissions from the patient rather than transmission to or through the patient.

In addition, a functional image does not necessarily provide structural information. Thus, a functional image is often evaluated with the help of an adjacent structural image. Computed tomography may be used for the structural image. Computed tomography is a transmission type of imaging. Transmission imaging refers to imaging where the imaging source (e.g., X-ray) is external to the subject and is transmitted through the subject to a detector. However, adjacent display may be confusing.

BRIEF SUMMARY

To provide application or study dependent information when reconstructing imaging data from one modality, data from at least a second modality is used in a multi-modal reconstruction. For example, bone information from CT is used for sharp bone tissue boundary segmentation, which segmentation is then used for SPECT imaging.

Figure 1:
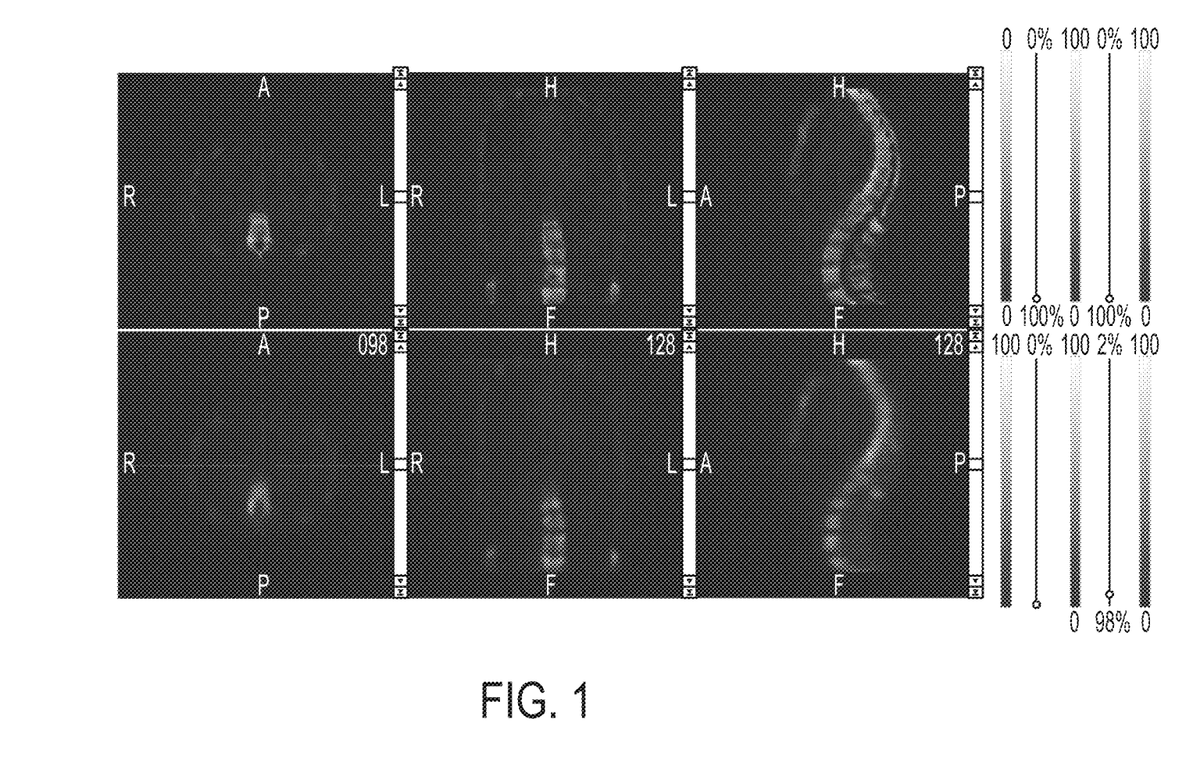
FIG. 1 shows example nuclear images with and without multi-modal reconstruction.

To provide more clinical content and enable better resolution and better represent structural information in functional imaging, multi-modal reconstruction may be used. For example, U.S. Published Patent Application No. 2010/0014730 teaches multi-modal reconstruction resulting in image quality improvement. The top row of FIG. 1 represents images from multi-modal reconstruction (SPECT+CT) and the bottom row represents images from nuclear imaging (SPECT-current clinical). Both rows of images were reconstructed with an iterative method, with 3D depth dependent resolution recovery based on collimator model, and with attenuation and scatter correction.

In multi-modal reconstruction, the anatomical information is segmented into zones. A zone is a 3D region of similar anatomical tissue. The segmentation is performed using an anatomical modality, such as CT. For example, bone tissue is segmented from non bone tissue. Segmentation is provided by simple thresholding segmentation, gradient analysis, filtering, random walker, or other image processing based on the CT. For CT, the segmentation is based on the measured units in CT, the Hounsfield (HU) scale. Bone segmentation based on HU is problematic since the HU value with the same attenuation properties of bone is not the same in different CT scanners, protocols, or even patients. The HU scale is a relative scale, with water as reference set to 0. Thus, any segmentation based on HU values alone may fail for water or soft tissues as the HU values may change, but not the threshold. Incorrect segmentation may be benign for attenuation correction in functional imaging since the half path length is >5 cm for a material at a typical isoptope energy, say for Tc99m at 140 keV is 1/Mu, with mu being the linear attenuation coefficient of that material. However, it degrades image quality when used in the multi-modal reconstruction, which uses the structural information to define sharp tissue boundary and thus is used in a different way than and in addition to attenuation correction.

By way of introduction, the preferred embodiments described below include methods, systems, instructions, and computer readable storage media for segmentation in multi-modal reconstruction of functional information. Rather than using HU values for segmentation, the HU values are converted into linear attenuation coefficients, such as in a μ-map (Mu map) using a scan adaptive conversion (see U.S. Pat. No. 6,950,494). The conversion uses different functions for different ranges of the HU values. Linear attenuation coefficients are less likely subject to variation by patient, protocol, or scanner. The resulting segmentation may be more consistent across various clinical settings, providing for more accurate multi-modal reconstruction.

In examples used herein, the extra modal information is segmentation oriented around bone. A bone tracer is used, so identifying different segments of bone or bone relative to non-bone is used. For other tracers and corresponding tissue types, the zones derived by segmenting from linear attenuation coefficients may be defined with different thresholds.

In a first aspect, a method is provided for segmentation in multi-modal reconstruction of functional information. Computed tomography (CT) data representing a region of a patient is obtained. The CT data is converted to linear attenuation coefficients. Locations in the region are segmented with the linear attenuation coefficients, where the segmentation is between at least five types of anatomical tissue resulting in the locations being assigned to zones segmented between respective types of the anatomical tissue. Separate zonal image objects are formed for each of the zones from the functional information. A processor reconstructs the functional information into an image object. The reconstruction includes separately forward projecting the functional information for each zone into data space. A contribution of each zone to a data model is weighted according to a zonal scaling factor for the respective zones. An image is generated as a function of the image object.

In a second aspect, a non-transitory computer readable storage medium has stored therein data representing instructions executable by a programmed processor for segmentation in multi-modal reconstruction of functional information. The storage medium includes instructions for generating a μ-map from computed tomography (CT) information, segmenting locations into different zones as a function of the μ-map, reconstructing from the functional information and the computed tomography information as a multi-modal reconstruction, the reconstructing being based on allocation of different amounts of signal to the different zones according to a contribution in each zone to the functional feature observed.

In a third aspect, a multi-modal medical imaging system is provided. A computed tomography system is configured to detect transmission through a patient. A nuclear medicine system is configured to detect emissions from the patient. A processor is configured to convert signals representing the transmission into linear attenuation coefficients for different locations in the patient, configured to establish at least three zones corresponding to at least three different types of tissues, respectively, from the linear attenuation coefficients, and configured to iteratively reconstruct an image object representing the patient from the detected emissions and the signals representing the transmission, the iterative reconstruction including separate forward projecting of the zones.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In multi-modal reconstruction, a functional image of an examined object is reconstructed by considering the spatial or spatio-temporal structure of the object when approximating the functional image according to the acquired functional data. The structure of the object allows separating the object into multiple zones. The volume within each of those zones is treated separately and equally in the reconstruction. Rather than equal treatment, the independence of the zones may be used for different treatment for different zones. Different amounts of signal are allocated to the zones according to the zone's contribution to the functional feature observed.

Multimodal imaging provides, in addition to the functional image data, the possibility to acquire information about the structure of the examined object. This information, also referred to as supplemental information, may include anatomical information about the imaged tissue (e.g., geometry and/or type), the movement of the tissue (breathing, cardiac movement), and/or the temporal behavior of the contrast agent/radioactive substance (flow, absorption, half-life). For example, high resolution CT imaging provides precise anatomical information about the examined object. Each organ or type of tissue is assigned to a separate zone.

When reconstructing an image object based on the functional image data and the support information, the contributions of the zones to the reconstructed image object may be optimized during the reconstruction and/or pre-assigned based on the supplemental information. Moreover, during the reconstruction, smoothing operations may be performed in a zone-specific manner. For example, smoothing is restricted to a zone and kernel functions are adapted to the geometry of a zone.

Multimodal reconstruction may impose a separation in anatomical zones of the reconstructed image object, but the zones do not modify the merit function of the applied reconstruction algorithm. The different zones are separately forward projected and renormalized as part of the iterative reconstruction. The zones may be defined based on the patient, scanner, protocol, radio pharmaceutical, or other factor that varies rather than zones based on attenuation along the line of response (i.e., rather than just attenuation correction). The result of multi-modal reconstructions may be increased resolution as compared to reconstruction with the functional information without multi-modal, even with attenuation correction.

The zones are automatically assigned. The assignment is based on the absorption coefficients provided by CT imaging. Since linear attenuation coefficients are absolute or measures of the tissue itself without or with little variance due to other factors, linear attenuation coefficients are used for segmenting.

The linear attenuation coefficients are determined from the absorption coefficients. Since CT data is output as HU, linear attenuation coefficients are calculated from the HU data. For example, U.S. Pat. No. 6,950,494, the disclosure of which is incorporated herein, teaches conversion of an HU image (i.e., CT data) to a μ-map (i.e., linear attenuation coefficients for different locations). The linear attenuation coefficients may be reliably mapped to different types of tissue using thresholding. A transition between zone boundaries may be smoothed. Segmenting based on the μ-map may be stable across clinical variance and less processing intensive than other segmentation.

Figure 2:
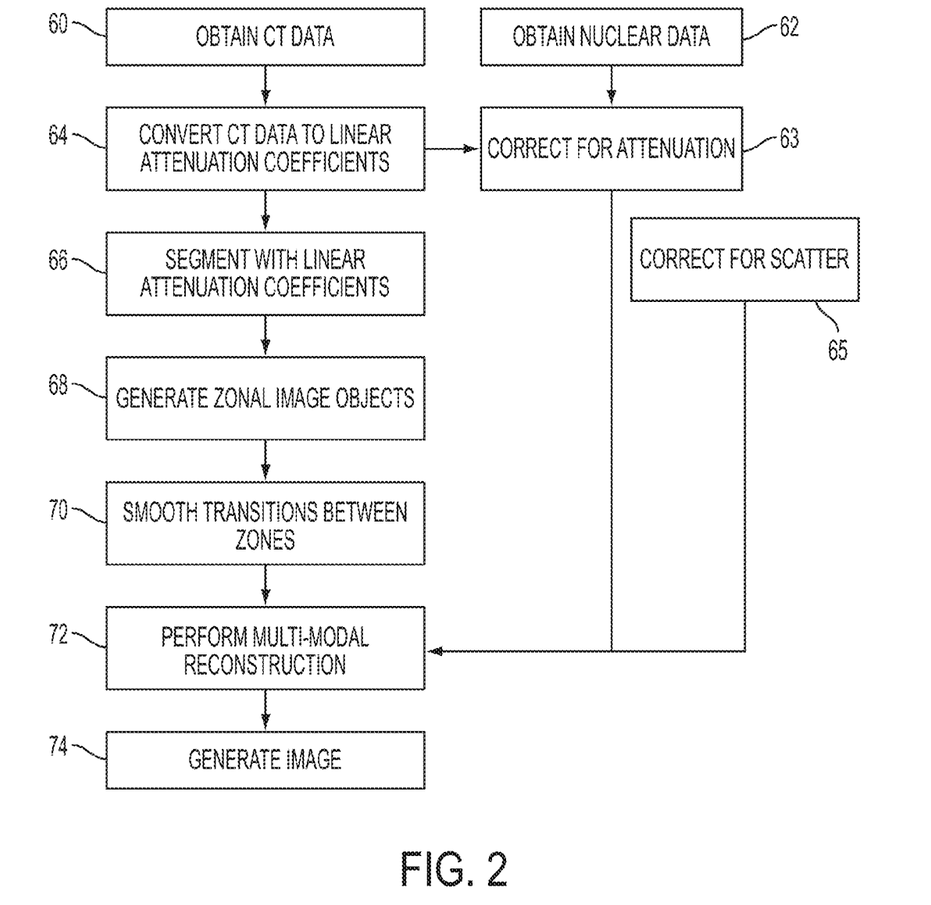
FIG. 2 is a flow chart diagram of one embodiment of a method for segmentation in multi-modal reconstruction of functional information.

FIG. 2 shows one embodiment of a method for segmentation in multi-modal reconstruction of functional information. The multi-modal reconstruction uses linear attenuation coefficients converted from CT data for segmentation.

Figure 6:
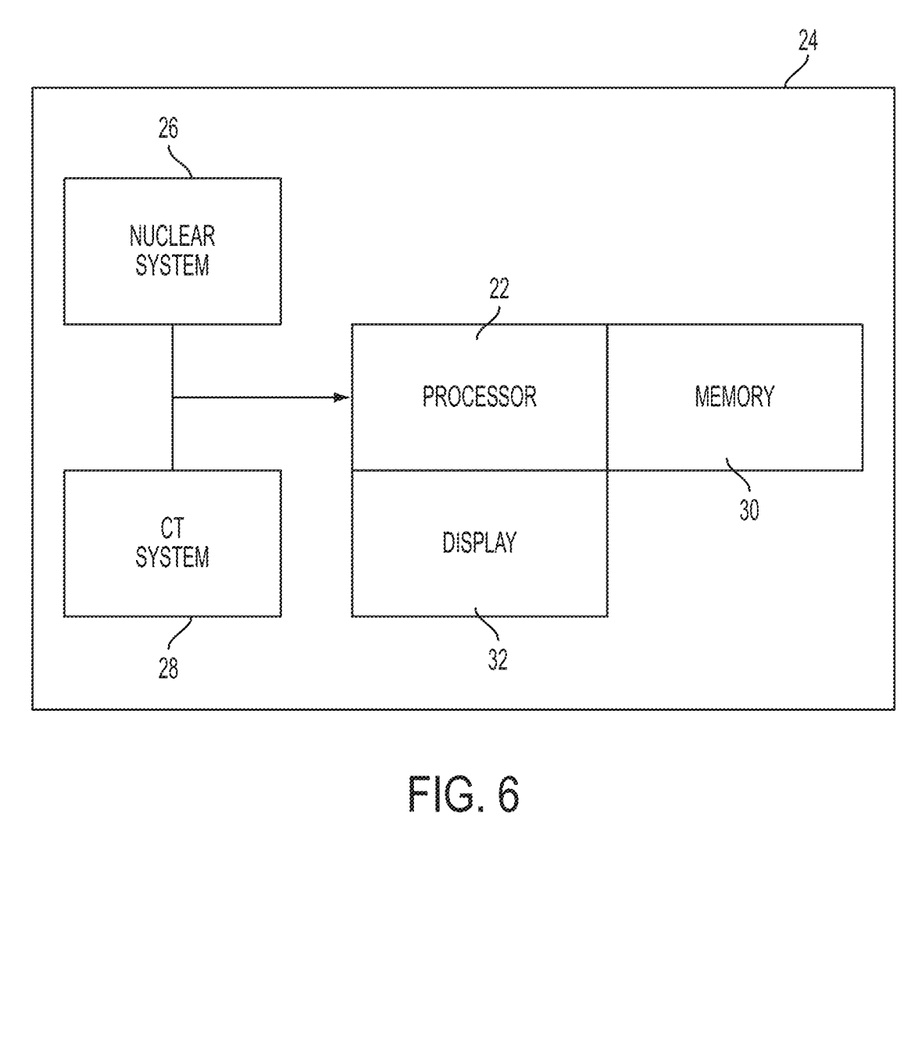
FIG. 6 is a block diagram of one embodiment of a system for segmentation in multi-modal reconstruction of functional information.

The methods of FIG. 1 is implemented using the system of FIG. 6, a processor, a computer, a CT scanner, a functional imager (e.g., nuclear scanner), and/or other device. The method is performed in the order shown, but other orders may be used. For example, the correction of attenuation of act 63 and/or smoothing of act 70 are performed as part of reconstruction (e.g., within the iterative reconstruction loop) in act 72 rather than prior to reconstruction. Additional, different, or fewer acts may be provided. For example, the attenuation correction of act 63 is not performed. As another example, the generation of the image in act 74 is not performed.

In act 62, nuclear data is obtained. SPECT, PET, or other nuclear scanning is performed on a patient. In alternative embodiments, other functional imaging is performed, such as fMRI or fCT.

The nuclear data is obtained from scanning, from data transfer, or from memory. A nuclear imaging system, such as PET or SPECT system, provides the nuclear data directly by scanning or indirectly by transfer or loading.

The nuclear data represents an examined area of a patient. The functional imaging system measures image data D of a functional process in the patient's body by using nuclear properties of matter. A radioactive substance, usually a disease specific biomarker, is administered to the patient, and the nuclear imaging system detects emitted radiation with a detector (e.g., with a ring detector for PET or with one or several gamma cameras for SPECT).

Raw data or preprocessed data is provided for multi-modal reconstruction. The multimodal reconstruction may use a system matrix H to describe the properties of the nuclear imaging system to iteratively improve a data model of an image object I representing the nuclear data D. The image object I may then be displayed using volume rendering or other imaging techniques.

The image object I, which is defined in an object space, is a reconstruction of the nuclear data D measured in a data space. The object space is the space in which the result of the image reconstruction is defined and which corresponds, for example, to the 3D volume (i.e., field-of-view or "FOV") that is scanned.

To provide higher resolution reconstruction, the nuclear data is separated into zones for the reconstruction. In act 60, support information S is obtained for creating the zones. The zones represent locations within the examined object and are derived from the support information S. The multimodal reconstruction R may improve the image quality and/or reduce the acquisition time of the functional imaging process by considering the zonal information in the reconstruction.

The support information S is obtained as computed tomography (CT) data. The CT data is obtained by scanning the patient, by transfer, or from memory. A CT scanner scans the patient using a protocol (scan sequence), such as by transmitting x-rays and detecting x-rays passing through the patient from different angles.

The CT data, reconstructed from the CT scanning, represents the same region of the patient as the nuclear data. The fields of view may be the same or different, such as overlapping. The CT data represents anatomical information about the examined object (e.g., shape, volume, thickness, and/or density of tissue types), type of disease and other disease specific features (e.g., density change within tissue (e.g. bone tissue), and/or calcification), type of application and other application specific features used to generate the image data (e.g., time dependence, and/or easily identifiable regions of lower interest but high signal (e.g. accumulation of a biomarker in the bladder)), and/or biomarker specific features (e.g., pharmacokinetic features, tissue types to which biomarkers attach, and/or time scale of processes for one, two, or more biomarkers).

The CT data and nuclear data are co-registered. A spatial registration between the support information and the object space of the nuclear measurement aids in assigning the object points in the object space of the functional data to their respective zones. One example registration, is to use a predetermined geometrical relation between the fields of view of the nuclear imaging device and the CT scanner, such as with a combined nuclear/CT system. In a second step, effects of patient motion during the two scans may be compensated using either a rigid or non-rigid body registration. The registration is then performed with reconstruction of the functional measurements alone. Anatomical CT data is co-registered with a preliminarily reconstructed functional image object.

The measurements for the CT data are Hounsfield measurements. X-ray CT images are calibrated so that each voxel is converted into units of Hounsfield, where each clinical scanner is calibrated for HU=0 for water. The clinical setting and/or calibration of the CT scanner may result in different HU values for the same tissue. In general for attenuation correction, a transmission scan is performed at an energy level other than the energy of the emission scan. The resulting attenuation map is to be scaled to the actual emission energy of the scan to correct for attenuation in the emission reconstruction process. For source-based derived μ-maps using discrete spectra, the conversion is simple because the discrete transmission and emission energies are known. For x-ray CT, the transmission spectrum is an attenuated Bremsstrahlung spectrum and thus continuous and depends upon the particular CT scanner and the attenuating body. The HU values are normalized for all scanners and protocols if the CT scanner for clinical practice has been properly set-up, so that water corresponds to HU=O and air corresponds to HU=−1000. Clinical CT scanners are calibrated using a vendor specific protocol to conform to this definition. However, there is no definition for densities greater than water. For instance, the same bone tissue may have different HU values when acquired with different CT scanners. The HU value of a bone specimen may even change depending on the surrounding amount of soft tissue and reconstruction parameters on the same CT scanner. Converting bone tissue accurately is important because it may contribute largely to attenuation of emission energy.

In act 64, the CT data is converted to linear attenuation coefficients. A μ-map is generated from the CT information. Linear attenuation coefficients may more accurately represent different types of tissue than absorption measures despite differences in patient, protocol, and/or CT scanner. The conversion adapts the structural or support information to the CT scanner, the patient, and/or the protocol.

Any conversion to a μ-map may be used. Linear attenuation coefficients are used in functional imaging for other purposes than defining zones. Attenuation correction is a prerequisite for quantitative nuclear medicine. CT data is used to derive linear attenuation coefficients suitable for compensating for attenuation along lines of response in the nuclear data. The same or different techniques for converting the CT data to linear attenuation coefficients may be used for zonal segmentation in multi-modal imaging.

In one embodiment, one of the conversions disclosed in U.S. Pat. No. 6,950,494, the disclosure of which is incorporated herein by reference, is used. For example, values of the CT data are each compared to a predetermined range. The predetermined range indicates air-soft tissue as CT scanners are typically calibrated to provide accurate HU values for air and soft tissue. When the value is within the predetermined range, a linear attenuation coefficient is calculated from the value using a linear function. The linear function is calculated from data points of air and water, for which the energy dependence is obtained from a fit to a double-power law. When the value is outside the predetermined range, the linear attenuation coefficient is calculated from the value using a different function, such as a linear fit from soft tissue and bone tissue with a constraint that the function is continuous over an entire range of Hounsfield units of the CT data. The conversion adapts to patient specific data and the varying parameters of the CT scan and reconstruction, eliminating the need for additional calibrations beyond clinically necessary or vendor specific CT scanner calibrations.

The scaling between the energy dependent linear attenuation coefficient and the HU, which are essentially water normalized differences between the attenuating material and water, may be approximated as piecewise linear functions for the transition between low Z (soft tissue) and higher Z (bone) materials. For water, the linearity is exactly based on the definition of the HU. Two or more regions may be considered, such as air-to-soft tissue (water) (HU<=O) and soft tissue (water)-to-bone (HU>O). The conversion from HU to linear attenuation coefficients is dependent upon emission-energy and transmission-energy. For instance, a CT image acquired at two different effective transmission energies ("tx") is scaled differently to the same emission energy. This difference in scaling occurs because of the different physical effects that contribute to the attenuation for varying energies at various amounts. For energies below 511 keV, the attenuation may be considered as a combination of both Compton scattering and photoelectric absorption. The higher the energy, the lower the contribution of the photoelectric absorption to the attenuation. At 511 keV, the contribution is essentially negligible for all biological materials (including bone). In the CT energy range (50-150 keV), however, the photoelectric absorption is not negligible.

The conversion mechanism is based on the fact that some types of media are always mapped onto certain HU values. CT pixel values are or are converted to HU values. CT devices may output pixel data a number of ways. Typically, a device outputs data in a proprietary fashion that must be converted to HU. The conversion is usually provided by the vendor. For example, CT devices may output Digital Imaging and Communication in Medicine (DICOM standard) compliant data containing a header that defines the conversion from proprietary pixel data to HU. If a CT device outputs pixel values as HU values, then the conversion is unity.

HU (bone) and the effective transmission energy are estimated. A "numerical observer" replaces the educated human observer. Any numerical observer function may be used, such as machine-learnt, database scoring, or statistical methods. In one embodiment, a histogram of the CT image volume is used to find the most common bone HU value at the given scan parameters in the CT image volume. This "effective" CT transmission energy includes all possible effects that could influence the bone HU, including effects from the CT reconstruction filter.

Conversion functions are created. The energy dependence of the linear attenuation coefficient may be fitted by a double-power law, with coefficients a, b, c for energies below and above a transition energy. Above the transition energy, Compton scattering is much more prevalent than photoelectric absorption for low-Z materials. The coefficients a, b, c are "weighted" based on empirical or theoretical information. The fit is done for below 150 keV and above 150 KeV, producing two sets of a, b, c values. The fit is "weighted" but not in the usual manner. Weights are typically derived from the variance of the error of a particular data point. In this case, weights have the effect that data points with larger measurement error don't "contribute" as much to the fit as data with a small error. This is used to "nail" the fit at the transition energy better, which in turn gives a fit which is a) continuous in the first derivative for all E in the energy range, and b) has very small deviation from all data points, but in particular at the clinically important energy region around 150 keV. The ratio of the weight at 150 keV with respect to all other weights at the other energy values is 1/10.

The main contribution to the attenuation coefficient comes from the varying cross sections of the photoelectric and Compton effects, which in turn also scale with changes around the chosen transition energy. This transition energy is chosen in part, because in nuclear medicine imaging, 150 keV is close to 140 keV, the TC99m emission energy (Tc99m is very often used in SPECT).

For iron (Fe), the transition energy is selected to be 250 keV, which is also fitted in a similar fashion. Although iron is a material that does not normally occur in the body, it is still found in many people (e.g., surgical nails, implants, bullets, wires, etc.), and thus, there may be a need to properly compute the linear attenuation coefficient.

The errors of the fit for the mentioned soft tissues and water are <0.2% and for bone are <0.55% for all energies.

The pixel value is checked to a predetermined range, between −1000 (HU for air) and 0 (HU for water). If so, processing proceeds to one function, and, if not, processing proceeds to another function.

For between air and water, air-soft tissue region is converted using a linear function F, calculated from the data points of air and water, for which the energy dependence is obtained from the above fit to the double-power law. Because air and water values on the HU scale are independent of the transmission energy, this conversion is accurate.

Soft tissue-bone approximation (HU>0) is more difficult. The HU value of bone is scanner, scan, reconstruction, and patient dependent and depends on the effective transmission energy, which is generally unknown. A human observer could identify the bone tissue in a CT volume and assign linear attenuation coefficients to this type of tissue, which is indexed by the HU values.

A conversion for all other values is then calculated using a conversion function for the soft tissue-bone region. The function is approximated by a linear fit to the data from soft-tissue and the identified bone tissue, with the constraint that the conversion function is continuous over the whole HU-range.

In alternative embodiments, other now known or later developed conversion functions may be used. Various approaches are known for converting CT values to linear attenuation coefficients, depending on the degree and type of approximation treating the continuous CT spectrum. These methods may be grouped in two major classes: uniform scaling and non-uniform scaling. In uniform scaling, pixels in the transmission slices are multiplied by the same factor K, where K is usually computed from the linear attenuation coefficient of water at the effective transmission-energy and emission energy. In non-uniform scaling, regions of the CT volume are defined as part of different classes of tissues ("segmentation"). Either each class of tissue is scaled from some "effective" transmission energy to the emission energy, or pixel values for each tissue type are replaced with the appropriate attenuation coefficients at the emission energy. Typical choices for tissue types include soft tissue, bone, lung, and air. Pixel-by-pixel conversion is an extension of the tissue typing approach. Each pixel is scaled from CT units to linear attenuation coefficients. In principle, this requires knowledge of the type of tissue for each pixel. This is often difficult because pixels may contain more than one tissue type ("partial volume") or an educated user may identify the tissue type of each pixel.

In act 63, the linear attenuation coefficients are used for attenuation correction. The nuclear data or other functional information results from emissions within an object being detected from outside the object. The gamma rays from the emissions travel through different materials or tissues. The tissues attenuate the gamma rays by absorption and/or scattering. Typically, attenuation correction accounts for bone and soft tissue separately. Locations of bone are assigned one attenuation coefficient and locations of soft tissue are assigned another attenuation coefficient. In other embodiments, measured linear attenuation coefficients along the path of travel are used. For a given line of response along the travel path of the gamma rays, different amounts of attenuation result depending on the tissues along the line.

The amount of attenuation along each line of response is determined. The nuclear data is adjusted to account for the attenuation. Attenuation correction is performed.

In act 65, the functional information is corrected for scatter. Photons from the object may be scattered. Scattering may be predominantly Compton scattering, whereby scattered photons loose energy. Scattered photons have changed the direction. For Compton scattering, the energy of the scattered photon depends on the scattering angle. Because the energy window width of the acquisition window is finite, the primary window contains photons that never scattered and thus indicates the direction of the source within the acceptance angle of the collimator. The primary window also contains scattered photons, all the way up to angles at which the energy falls below the lower energy bound. The counts in the projection data are thus contaminated with photons of directions that are undetermined under given constraints, and thus reduce contrast and increase noise in the reconstruction.

The effects of scattering may be, in part, corrected. Any scatter correction may be used. The scattering content and distribution in the primary photon data set is estimated for energy based window scatter estimation. For example, the scatter projection estimate is found according to a TEW method. The SPE is used additively in the forward projection.

In act 66, the linear attenuation coefficients are used for segmenting. This use of linear attenuation coefficients is different than attenuation correction. Attenuation correction accounts for the physics of gamma rays passing through tissue. Different types of material may attenuate differently and the simplification to bone and non-bone may even group locations. However, the attenuation correction alters the amplitude of the detected nuclear data and is not used as zones in multi-modal reconstruction. The multi-modal segmentation, even if the same segmenting is used for both, is provided for separately forward projecting the functional information by zonal image objects. This is in addition to attenuation correction. In other embodiments, attenuation correction is not performed.

For multi-modal reconstruction, different locations are assigned to different types of tissue. The locations associated with the same type of tissue or group of types form a zone. In general, a zone includes object points with similar features. A zone need not be an enclosed area. The zone is continuous or discontinuous. The zones define spatial regions associated with a given grouping of one or more types of tissue. One zone may represent a target organ or target tissue of the biomarker used for the functional image.

Any number of types of tissue may be used. For example, bone and non-bone groupings are used. As another example, three types corresponding to bone, soft tissue, and lung are used. In one embodiment, at least five types of anatomical tissue are segmented as separate groupings. Dense or cortical bone, soft bone, soft tissue, adipose, and lung are one example of five zones. Bone or other tissue may be further decomposed, such as grouping locations associated with different bone density into different zones.

Figure 3:
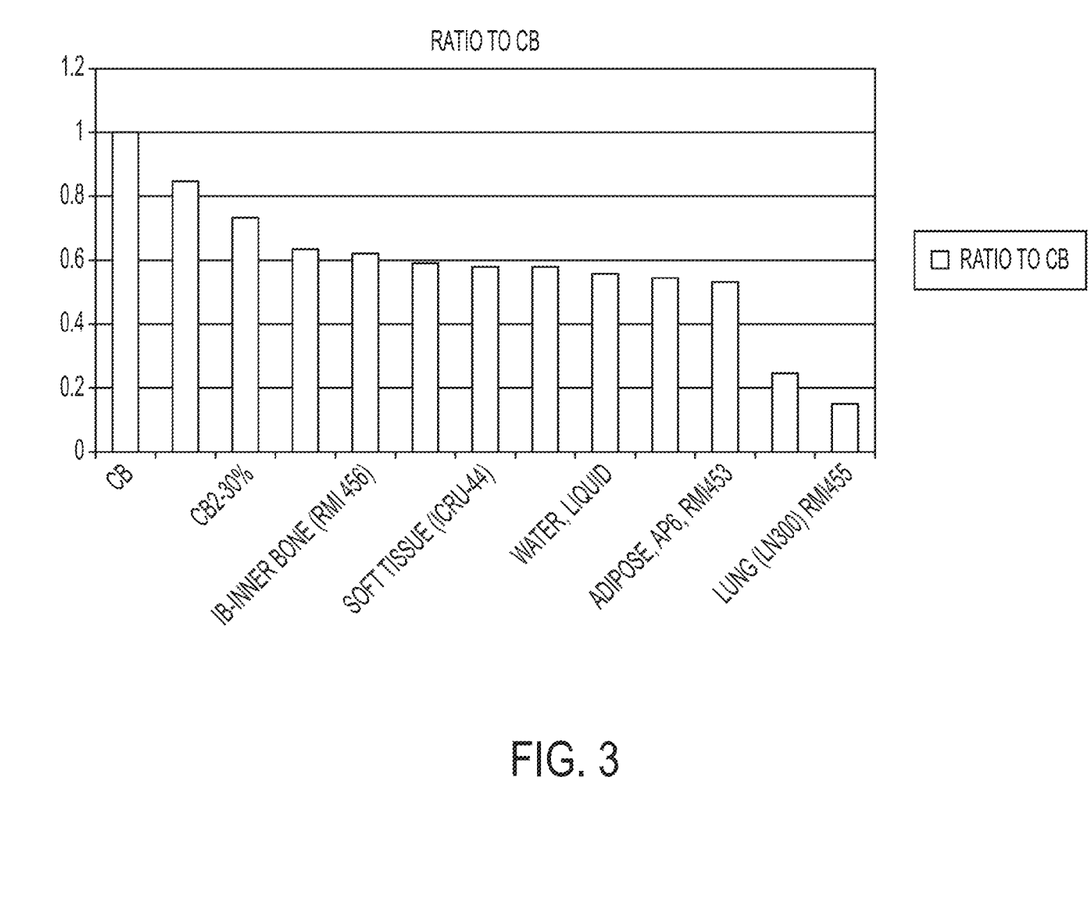
FIG. 3 is an example bar graph showing ratios of different possible zones and corresponding types of tissue to cortical bone.
Figure 4:
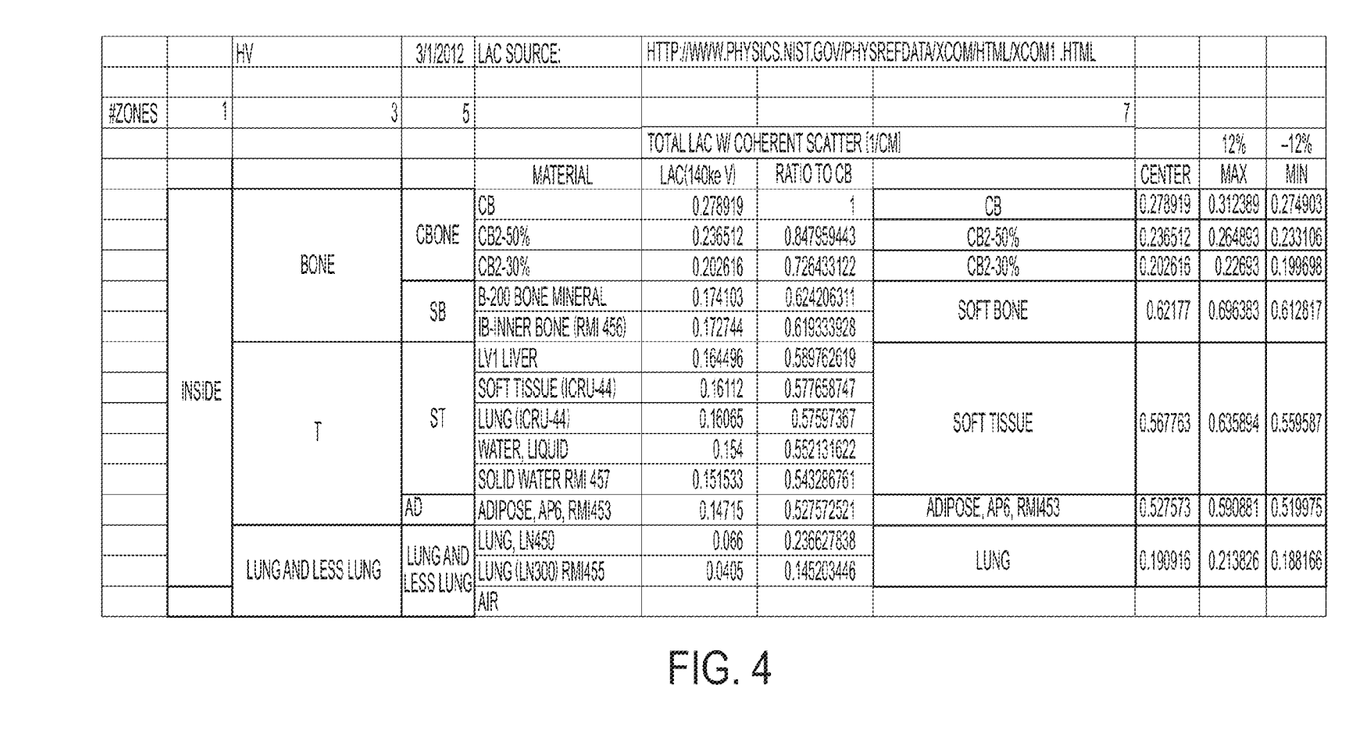
FIG. 4 is an example table of zones and corresponding linear attenuation coefficient thresholds.

FIG. 3 shows ratios of linear attenuation coefficients relative to cortical bone. Some ratios are similar, suggesting groupings of the types of tissue into a same general type. Other ratios are distinct, suggesting a group of just one specific type of tissue. For example, FIG. 3 shows seven different types with text labels across the bottom, including three distinct types relative to bone. FIG. 4 shows two, three, five, and seven zone separations and corresponding linear attenuation values. Any number of types of tissue and corresponding zones may be used. By considering the radiopharmaceutical, type of scan, disease of interest, or other consideration than type of tissue, other zone separations may be used.

The zonal information is derived by automated analysis of the support information and corresponds to a separation of the object space in two or more spaces. Another zone may be provided as a null zone for locations surrounding, but not within the examined object. A given field of view may include fewer than all the zones being used for segmentation. A type of tissue for a zone may not exist in the field of view. The segmentation may test for the type of tissue or group of tissues and determine that there are no locations for that zone.

To segment, the linear attenuation coefficient for each location is compared with one or more thresholds. The thresholds separate the anatomical tissue by type. Pairs of thresholds may separate one type from another. Alternatively, the closest threshold to the linear coefficient is located to indicate the type.

Figure 5:
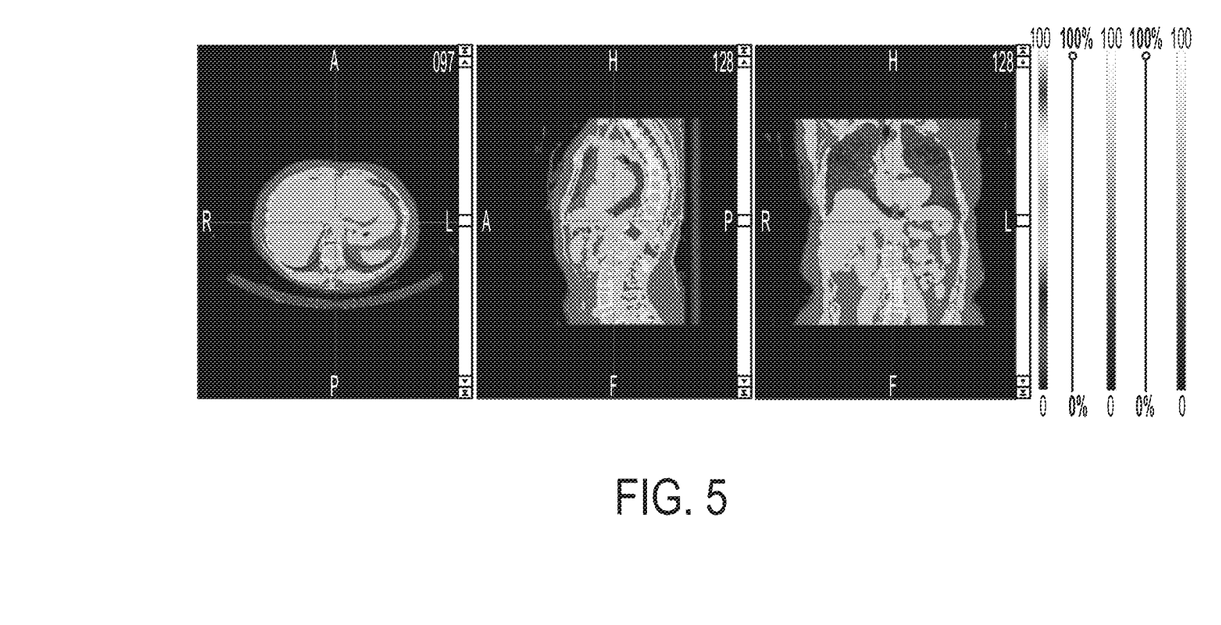
FIG. 5 shows three example distributions of linear attenuation coefficients and the corresponding zones.

Similar absorption coefficients ($\mu$-values) derived from a CT scan are used to determine zones. The information about how the object space is separated into zones is referred to as zonal information. FIG. 5 shows a gray scale mapping of zones. Different zones are shown with different shades of gray based on thresholding to identify the type of tissue from the linear attenuation coefficient. The zone planning view of FIG. 5 includes a coronal view, a sagittal view, and a transverse view of various zones that have been assigned with different grey scale values. The object space is separated into zones or locations assigned to different groups based on anatomical structure and/or other considerations.

More complex differentiation may be used, such as including uptake information from a preliminary functional reconstruction. In other embodiments, nuclear data is also used when separating the object space into zones. For example, an intensity value of a preliminary reconstructed functional volume additionally distinguishes tissue with similar linear attenuation coefficients but with different affinity to a radioactive substance.

The zonal information is provided as a zone-function $z(r)$. The zone-function is a functional presentation, indicating position(s) and shape(s) in object space. Another presentation of a zone-function is an object defined in the dimensions of the object space that as an entry for an object point includes the degree of affiliation of that object point to the respective zone. The definition of zone-functions as an object in object space allows projecting the zone (here the zone-function) onto any object by matrix multiplication.

In act 68, separate zonal image objects are generated for each of the zones. The functional information, such as the obtained nuclear data, is grouped by locations for the zones during reconstruction. Based on the zonal-information, zonal image objects are prepared. Only the object points within the zone corresponding to the zonal image object contribute to the reconstruction of the image object. During the reconstruction, the values of object points outside the zone do not contribute to the reconstruction of the zonal image object. Such values are constrained to be zero because one assumes that those object points do not generate any detected signal. The zonal image objects are generated for separate forward projection.

As an example for restricting the contribution of the zonal image object to its zone, a zone-function $z(r)$ assigns values greater than zero to all object points at least partly affiliated with the respective zone. For example, in an object representing the zone-function, the value 1 is assigned to object points having a $\mu$-value within a predefined range of $\mu$-values and a value of 0 to object points outside that range. To allow a smooth transition between zones, the zone-function may have values between 0 and 1 for border object points. For example, a ramp of width δμ is provided at a limiting μ-value in which the zone-function reduces from the value of 1 to the value 0.

Multiplication of any object in object space with a zone-function restricts the entries of the object to be non-zero only at object points that are affiliated with the respective zone. If, during the reconstruction, object points outside the zone are assigned with non-zero values, a repeated multiplication with the zone-function may be used to set those values to 0.

The generation of zonal information from the support information (linear attenuation coefficients) is performed by first identifying features of the examined object that relate to the functional measurement and then identifying the object points having the respective feature. In general, the areas defined by the zones abut each other. Smooth transitions may be enforced between zones.

To consider multiple zones (e.g. N zones) in a mathematical description, an image object $I_\alpha$ defined by the functional activity density of the complete object space is a sum over N zonal image objects $\psi_\alpha^{(n)}$, ($n=0, \ldots, N-1$), each representing a functional image of a zone, wherein each zonal image object $\psi_\alpha^{(n)}$ is multiplied by a respective structural zone-function $z_\alpha^{(n)}$.

$$I_\alpha = \sum_n z_\alpha^{(n)} \psi_\alpha^{(n)}.$$

The zone-function may be purely spatial and define the geometry of a zone in three spatial dimensions. The zone-function may be spatio-temporal. In general, the index α stands for all variables that characterize the functional activity. For example, in nuclear imaging, α stands for the spatial coordinates of an object point, the time at which a photon is been detected, and the energy of the detected photon. α is usually discretized into 3D voxels and time and energy bins. Often, α is referred to generically as a "voxel," although additional time and energy components may be provided.

The functional zonal image objects $\psi_\alpha^{(n)}$ are determined from the multimodal reconstruction such that each zonal image object $\psi_\alpha^{(n)}$ represents the functional activity in the respective zone as well as possible. The structural zone-functions $z_a^{(n)}$, on the other hand, are predetermined from the linear attenuation coefficients and are generally not modified in the reconstruction. The zone-functions $z_a^{(n)}$ designate the position and form of the zones (as functions of time and energy) and satisfy the condition $$\sum_n z_\alpha^{(n)} \leq 1 \forall \alpha.$$

Most voxels belong to no more than one zone. So for most object points α, $z_\alpha^{(n)}=1$ for some n, and all other zone-functions vanish, $z_a^{(n'\neq n)}=0$. As zones may overlap, border voxels in the area of overlap between zones may be attributed to more than one zone, so there can be several values of n for which $z_a^{(n)}<1$. Zones may also taper off gradually at the edges of the examined object or at an interface with an implant, which like the outside of the patient does not have any functional activity and may be considered as a null zone. For border voxels that overlap with a null zone, the contribution of a voxel may be less than 1, such as the sum $$\sum_n z_\alpha^{(n)} \leq 1$$

is less man 1.

In act 70, the zone boundaries are smoothed. Any smoothing function may be used to taper the contribution of edge locations and/or edge linear attenuations relative to the zone. For example, the transition in zone boundaries is modeled as a smooth transition. The zones are used as weights where locations within the zone are weighted as a 1 value and locations out of the zone are weighted as 0 values. For locations that are similar but not at the linear attenuation threshold (i.e., boundary locations), a weight in-between 1 and 0 may be used. For example, tissue with a linear attenuation coefficient in a range in between two thresholds is boundary locations. The zonal weight used for these boundary locations may be less than 1, but greater than 0.

One possible boundary smoothing is a 3rd order polynomial. The inflection point center is at the mid of the centers of tissue classes (e.g., threshold point) and slopes of zero at the centers (i.e., an s curve over linear attenuation coefficients). Other smoothing functions may be used.

In act 72, the functional information is reconstructed into an image object. A processor reconstructs the image object from a combination of the functional information and the CT data. In one embodiment, the multi-modal reconstruction described in U.S. Published Patent Application No. 2010/0014730, the disclosure of which is incorporated herein by reference, is used.

In conventional functional imaging, functional and anatomical images are reconstructed separately and are only presented together (e.g. as overlaying or adjacent images) to the diagnosing physician. However, the resolution and image quality of the functional and anatomical images is determined by the respective reconstruction algorithms associated with the functional and anatomical imaging techniques. Sometimes, nuclear imaging techniques use an attenuation map (also referred to as μ-map) derived from a CT scan to compensate for signal loss within the examined object, but without altering the resolution of the nuclear imaging.

In contrast, the multimodal reconstruction R uses zonal information derived from the support information S. The support information S provides structural information about the measured object such that the object space is divided in multiple zones. For each such zone, the reconstruction of the image object is constrained by using a zonal image object. Each of the zonal image objects may be treated differently in the reconstruction but the zonal image objects are used together to, for example, generate a data model of the reconstructed image object I. A zone-specific operation is, for example, a smoothing operation that is performed on individual zonal image objects.

Support information S may further relate to the energy and event time of the detected photons. Thus, a zone may also be based on those parameters. For example, a 4D zone considers temporal changes of the position and/or shape of a zone, which is caused by any kind of movement of the object (e.g., breathing and heart activity). Accordingly, the object space may include additional (non-geometric) dimensions when appropriate.

In general, the reconstruction is performed using the signal associated with a zone as an additional parameter or an additional constraint, while the spatio-temporal structure of the zones is preserved. Methods to provide zone-specific constraints include performing specific measurements, estimating the constraints based on imaging data, or providing predetermined constraints in a medical database, which contains information about the constraint (e.g., for various diseases, radioactive materials, biomarkers, and patient parameters such as age, sex, height, and weight). In nuclear imaging, predetermined uptake expected for a zone (herein also referred to as fractions) may also be used as a constraint for the zones.

To measure the zone-specific constraints, an unconstrained pre-reconstruction of the image data is performed. The fractions are determined from the uptakes measured in a zone. Determining the fractions from the image data is less susceptible to deviants than reading values from a database that may not always be appropriate for the current nuclear measurement. However, the values for the fractions of the uptake depend on the quality of the pre-reconstruction and an error in the constraints may propagate into the multimodal reconstruction.

Another method of determining constraints includes assigning to each zone a value $c_n$ constant for all object points and performing an optimization process based on a merit function, such as Poisson maximum-likelihood or Mighell's modified chi-square gamma, that optimizes the coefficients $c_n$ that represent the constraint (e.g. the relative uptake). This optimization is referred to herein as renormalization.

The constraint provides for allocation of different amounts of signal to the different zones. The signal is allocated according to a contribution of each zone to the functional feature observed.

An iterative reconstruction of the image object is performed. The reconstruction may, for example, include assigning the zones to the object space, reading functional image data, back-projecting the image data and generating zonal image objects, assigning linear coefficients (zonal emission fractions) to the zones, forward projecting each zone separately and generating zonal projections as zonal data models, calculating a total projection of a complete data model as a linear combination of the zonal projections, performing a fit to derive the best linear coefficients, renormalizing the zonal emission and the zonal projection by the new linear coefficient, and checking for goodness-of-fit of the reconstruction. If necessary, the process is repeated until a sufficient goodness-of-fit is achieved or a maximal number of iterations is reached. At the end, the reconstructed image is output. In other embodiments, additional, different, or fewer steps are performed in the process. For example, the zones are usually only assigned once at the beginning of the multimodal reconstruction and the coefficients may be assigned immediately after assigning the zones.

Introducing zones enables further smoothing of a zonal image object. The smoothing operation is zone-specific. Any smoothing may be used.

In the following, a mathematical description for specific algorithmic features is given for multizone multimodal reconstruction. The reconstruction includes zonal renormalization operations, an update operation, and a recombining operation. In functional imaging, image reconstruction estimates a best value for each object point to resemble the functional activity density as accurately as possible. The image reconstruction is based on the measured image data D and a data model m derived from a reconstructed image object with the help of a system matrix H and a merit function. The zonal renormalization operations and the update operation compare the measured image data D and a data model m and then use the system matrix H to transform the image object from object space to a data model in data space.

The algorithm begins with a set of N initial zonal image objects $I_{\alpha,initial}^{(n)}$, each having the dimension of the final reconstructed image object. The initial zonal image objects $I_{\alpha,initial}^{(n)}$ are derived from the functional image data by a first back projection that creates a first estimated image object and applying zonal information (e.g., multiplying a first estimated image object with zonal functions). Alternatively, the zonal image objects are initialized arbitrary, such as setting all initial zonal image objects identically to unity.

The renormalization operation generates an initial (iteration) input object comprising those initial zonal image objects $I_{\alpha,initial}^{(n)}$ for each zone. In addition, the initial input object comprises an initial scaling factor $c_n$ for each zone and therefore, for each initial zonal image object $I_{\alpha,initial}^{(n)}$. The scaling factors c constitute a zone-specific constraint for the reconstruction. In one example, a scaling factor corresponds to an initial estimate of the fraction of the signal uptake in its particular zone.

The update operation is repeated in an iterative reconstruction loop characterized by an index iteration that is increased for each new iteration step. For each iteration, the output of the update operation is an output object of updated output zonal image objects $I_{\alpha,output}^{(n)}$. These output zonal image objects $I_{\alpha,output}^{(n)}$ usually include a modification for each object point with respect to the initial zonal image objects $I_{\alpha,initial}^{(n)}$. The update operation does not modify the scaling factor $c_n$.

The iterative reconstruction loop includes a decision operation that evaluates whether another iteration step needs to be performed or not. If another iteration step is performed, then the output object is used to update the initial scaling factor c by the renormalization operation, thereby providing an updated scaling factor $c'_n$. Together, the updated scaling factor $c'_n$ and the updated zonal output object $I_{\alpha,output}^{(n)}$ act as a next input object for the subsequent iteration step.

If the evaluation determines that the iterative reconstruction is ended, the scaling factor $c'_n$ may be updated a last time to generate scaling factor $c''_n$. A last renormalization operation may be performed based on the zonal image objects $I_{\alpha,output}^{(n)}$ of the last output object, or of any previously determined output object. The output zonal image objects of the selected last output object and the scaling factors c" form the final output object from which the recombining operation derives the reconstructed image object I.

During the multizone multimodal reconstruction, a zonal forward projection operation between object space and data space generates, for example, a data model m of an image object. Specifically, zonal forward projection operations are used within the algorithm for evaluating the zonal image objects or for calculating parameters of the update operation.

In image reconstruction, object space and data space are related to each other through the system matrix H of the functional imaging system. Thus, for any projection operation, the system matrix H and its transpose $H^T$ are used to transform objects between object space and data space.

In general, a forward projection is an application of the system matrix H to an object in object space. The result of a forward projection is a "projected object" in data space. As an example in nuclear imaging, a forward projection is the linear operation that transforms the functional activity density into the total data model $m_i$ of predicted detection events:

$$m_i = \sum_\alpha H_{i\alpha} I_\alpha.$$

Here, i stands for the 2D detection positions on the detector system of the functional imaging system, as well as for the detection time t' and energy E'. In general, the detection time and energy of a photon does not need to be the same as the emission time t and energy E. Such cases arise, for example, in PET with time-of-flight corrections, or when the photon energy is changed in a scattering event. In many cases, however, these differences may be ignored, and t'=t and/or E'=E. A photo peak energy window may then include scattered photons, whose estimated contributions $s_i$ are estimated separately. A data model $m_i$ based on a forward projection and scatter correction may be written as:

$$m_i = \sum_\alpha H_{i\alpha} I_\alpha + s_i.$$

The system matrix H is rarely applied directly as a matrix multiplication. Instead, it is represented as a product of operators $H_n$:

$$H = H_n \otimes \ldots \otimes H_2 \otimes H_1$$

Corresponding to the forward projection, the backward projection from the data space into object space may be described as an application of the transpose $H^T$ of the system matrix H:

$$I_\alpha = \sum_i H_{\alpha i} m_i$$

The transpose $H^T$ is also rarely applied as a matrix multiplication. Instead, it is represented as a product of operators:

$$H^T = H^T \otimes H_2^T \otimes \ldots \otimes H_n^T$$

In the multizone multimodal algorithm, forward and backward projections are used. One example for a backward projection is the generation of the first estimated image object for the initial zonal image objects. Also an ordered-subset-expectation-maximization (OSEM) algorithm uses a forward projection to generate the data model, which is then used to derive update factors in data space. Those update factors are then back projected to generate an update object in object space that is used to update the input object. An algorithm based on a non-negative least-squares (NNLS) algorithm also uses a forward projection to generate the data model. Backward projections are used when determining an auxiliary gradient, specifically, when calculating the preliminary auxiliary gradient and the preconditioner object.

When reconstructing multiple zones, the input object for a zonal forward projection operation comprises more than one zonal input object. A zonal forward projection is adapted to the multizone situation and includes a forward operation, applied separately to each zonal image object of each zone. The zonal forward projections consider, thereby, the contribution of each zone to the image model. Specifically, the zonal forward projections use the zone-functions $z_\alpha^{(n)}$ to represent the zone-specific contribution. Any stray values that the zonal image object may have received at object points outside its specific zone due to the update operation are multiplied by zero or other value according to the specific definition of each zone-function. Thus, based on resulting zonal data models $m_i^{(n)}$ $$m_i^{(n)} = \sum_\alpha H_{i\alpha} z_\alpha^{(n)} \psi_\alpha^{(n)} \forall n$$

The total data model $m_i$ is represented by a sum of the zonal data models, plus a scatter estimate:

$$m_i = \sum_n m_i^{(n)} + s_i.$$

A zonal forward projection considers the zone-functions $z_\alpha^{(n)}$, the scattering corrections $s_i$, and the scaling factors when determining a scaled data model $m_i^{scaled}$. The scaling factors $c_n$ include the zone-specific constraints, such as the fractional contribution of each zone to the final image object. The scaling of the zonal images with the scaling factors $c_n$ transforms into scaling the zonal data models with the same zone-specific scaling factor $c_n$.

The zonal renormalization process is applied at multiple positions within the iterative reconstruction algorithm. However, the renormalization does not need to be performed at every position indicated or for every iteration step. The renormalization may be based on a calculation and optimization of the merit function, which usually optimizes the image data D, the zonal image objects $I_\alpha^{(n)}$, their corresponding scaled data model $m_i^{scaled}$, the zone-functions $z^{(n)}(\alpha)$, and the respective scaling factors $c_n$. The forward projection operation is the basis for the calculation of a total scaled data model $m_i^{scaled}$. The zone-functions $z_\alpha^{(n)}$ are derived by analyzing the support information S. The zonal image objects $I_\alpha^{(n)}$ are the constant initial zonal image objects or any updated zonal image objects calculated by the update operation.

The merit function is optimized for the scaling factors $c_n$, which in general are an optimization of only few parameters (e.g., the N scaling factors $c_n$). The number N of zones into which the object space is usually separated is in the range from 2 to about 50, for example, 3, 4, 5, 10, 15, 20, 25, or 30. The output of the zonal renormalization process includes an optimized scaling factor $c'_n$ for each zonal image objects $I_\alpha^{(n)}$.

The scaling factors c influence the data model. Scaling of the zonal image objects $I_\alpha^{(n)}$ with the non-negative scaling factors $c_n$:

$$\psi_\alpha^{(n)} \to c_n \psi_\alpha^{(n)} c_n \geq 0 \; \forall n$$

leads to corresponding scaling of the zonal data models $m_i^{(n)}$:

$$m_i^{(n)} \to c_n m_i^{(n)} \forall n.$$

The scaled total data model $m_i^{scaled}$ as generated by the zonal forward projection, including scaling and scattering correction, is given by modifying the sum in $$m_i = \sum_n m_i^{(n)} + s_i,$$

as follows:

$$m_i^{scaled} = \sum_n c_n m_i^{(n)} + s_i.$$

During the zonal renormalization operation, the scaling factors $c_n$ are chosen to minimize a merit function of the data D given the total data model $m_i^{scaled}$. For example, a modified chi-square-gamma statistic is used. The chi-square-gamma statistic of Mighell is defined by:

$$\chi_\gamma^2 = \sum_{j=1}^{J} \frac{(d_j + \text{Min}\{d_j, 1\} - m_j)^2}{d_j + 1},$$

wherein $d_j$ and $m_j$ are the j-th entries of the measured data set D and the data model m, respectively. J is the number of data points in data space or the number of data points in the data set D.

Mighell's modified chi-square-gamma statistic is unbiased and well behaved for low counts. The statistic also is quadratic in the optimization parameters, so setting its gradient to zero results in linear equations for them, albeit constrained to non-negative $c_n$.

In one embodiment, a conjugate gradient method is used with a preconditioner. The negradient, linear in the image, is represented as:

$$G_\alpha = -\partial L/2 \partial l_\alpha = \sum_i H_{i\alpha}(d_i+1)^{-1}(d_i + \text{Min}(d_i, 1) - s_i) - \sum_{i\beta} l_\beta H_{i\beta}(d_i+1)^{-1} H_{i\alpha}$$

with a weighted gram matrix:

$$Q_{\beta\alpha} = \sum_i H_{i\beta}(d_i+1)^{-1} H_{i\alpha}$$

The preconditioner modifies negradient and is represented as:

$$\tilde{G}_\alpha = G_\alpha / \sum_{i\beta} H_{i\alpha}(d_i+1)^{-1} H_{i\beta}$$

An alternative merit function is the log-likelihood function:

$$L = 2 \sum_i [m_i^* - d_i \ \text{Ln}(m_i^*)],$$

The log-likelihood function is not well behaved at low counts.

Renormalization of the constant initial objects (with value 1 for all α) retains constant initial zonal images $I_{\alpha,initial}^{(n)}$ that vary from zone to zone according to their scaling factors. The zonal image objects $I_\alpha^{(n)}$ and the scaling factors $c_n$ are considered as parts of the input objects and the output object. Renormalized zone-functions may be provided only to the iteration loop, such as by substituting $I_\alpha^{(n)}$ with $c_n I_\alpha^{(n)}$. For the initial zonal image object, $I_\alpha^{(n)} \equiv c_n$. Those scaled zonal image objects are also updated whenever updated scaling factors are available.

Performing the combining operation on the initial zonal image object results in an image object I that is piecewise constant, with intermediate values at zone boundaries:

$$I_\alpha = \sum_n c_n z_\alpha^{(n)}.$$

Zonal renormalization operations during the iterative reconstruction operation update the scaling factors in view of improved zonal image objects. Thus, those zonal renormalization operations allow the constraints for the different zones to change from one iteration to the next. This update of the constraints may reduce or avoid serious artifacts, which may be generated otherwise. Usually, the scaling factors do not change much after several iterations.

Iterative reconstruction allows the zonal image objects to vary spatially. The update operation of the reconstruction proceeds much as in a conventional "unimodal" reconstruction, except that the scaled total data model $m_i^{scaled}$ is used and that zonal renormalization may be performed before zonal image objects are forward projected.

The image object resulting from multi-modal reconstruction has a greater resolution than reconstructing without the combination due to a resolution of the CT data, as represented in FIG. 1 (compare top row to bottom row). The multimodal reconstructed image shows functional activity with increased anatomical accuracy. Thus, multimodal reconstruction uses the anatomy of the examined object when reconstructing the functional image object. In an example, multimodal reconstruction uses the distribution of a target tissue of a biomarker (e.g., a specific organ or a bone) when reconstructing the functional density of that biomarker that primarily accumulates within that target tissue.

In multimodal reconstruction, the resolution of the support information may affect the resolution of the functional image object and the sensitivity of the functional process. Within a zone, the functional resolution and sensitivity may prevail. For example, along the extension of the bone shown in FIG. 1, the resolution is governed by the functional modality (e.g., by SPECT or PET). However, across a zone, such as at the interface of the bone with surrounding tissue, the resolution may be improved to that obtained using the support modality (e.g., the high resolution of a CT system). Thus, multimodal reconstruction may allow quantitative functional imaging of a predetermined zone. One example of such a predetermined zone is a zone selected to encompass one or more anatomical structures.

The zonal reconstruction transfers the benefits of the relatively high-resolution of structural imaging technique to the relatively low-resolution functional imaging techniques, thereby increasing, for example, the resolution of the functional images. In addition or alternatively to the increased resolution, the functional imaging may be performed with lower signal. For nuclear imaging, this allows imaging with lower count rates with the benefit of a lower radiation dose for the patient.

In act 74, an image is generated. The image object is a three-dimensional representation of the detected emissions of the patient. The image object is rendered or otherwise used to generate an image. For example, a multi-planar reconstruction or single slice image of a plane is generated. The intersection of one or more planes with the image object is visualized. As another example, a surface or projection rendering is performed for three-dimensional imaging. Other imaging may be used.

One image is generated. Alternatively, a sequence of images is generated. For example, image objects from different time periods are used to generate a sequence of images representing the patient over time.

The image of the functional information from the multi-modal reconstruction is displayed alone. Alternatively, an anatomical image is displayed with the functional image. For example, the functional image is overlaid on a CT image. The overlay may be colored for display on a gray scale CT image. Other combinations may be used.

FIG. 6 shows one embodiment of a multi-modal medical imaging system. The system 24, using hardware, software, or hardware and software, segments using linear attenuation coefficients converted from absorption measures. The segmentation is used in multi-modal reconstruction of functional information.

The system 24 includes a processor 22, a nuclear imaging system 26, CT imaging system 28, a memory 30, and a display 32. Additional, different, or fewer components may be provided. For example, a functional MR imaging system is provided instead of the nuclear imaging system 26. In one embodiment, the processor 22, memory 30, and/or display 32 are part of one of the nuclear imaging system 26 or the CT imaging system 28. In alternative embodiments, the processor 22, memory 30, and/or display 32 are provided as a workstation or computer separate from the imaging systems 26, 28. The memory 30 is part of a computer or workstation with the processor 22 or is a remote database, such as a picture archiving and communications system (PACS).

The CT imaging system 28 is an x-ray source and detector mounted on a moveable gantry. The CT imaging system 28 is configured to detect transmission through a patient. The x-ray source generates x-rays, some of which pass through the patient. The detector detects the transmitted x-rays that pass through the patient. The energy used, timing, scan angles, and/or other aspects of the CT scan are set for a patient and used to scan a volume or other region of the patient. Any now known or later developed CT imaging system 28 may be used. While "imaging" is used herein, the CT imaging system 28 may be used to acquire data representing the patient without generating or displaying a CT image.

The nuclear imaging system 26 is any now known or later developed nuclear medicine system, such as PET or SPECT scanner. The nuclear imaging system 26 includes a detector for detecting emitted radiation from within the patient. For SPECT, a gamma camera is used to detect. For PET, the detector is an array of photo multiplier tubes or silicon avalanche photodiodes. The detector detects positron emissions. The positron is emitted from a tracer or radiopharmaceutical. The positron interacts with an electron near the location of emission, generating gamma rays propagating at about 180 degrees apart. The gamma rays are received by or travel to the detector. Crystals connected with the detector convert the gamma ray or other radiation into light. The detector detects the light.

The detectors are arranged in a block or ring. Multiple blocks of detectors may form a ring or part of a ring around a patient space or bore. By at least partially surrounding the bore, different events may be detected by different detectors. A given detector may detect a sequence of events from the same or different locations of the patient.

The processor 22 is a general processor, central processing unit, control processor, graphics processor, digital signal processor, application specific integrated circuit, field programmable gate array, amplifier, comparator, time-to-digital converter, analog-to-digital converter, digital circuit, analog circuit, timing circuit, combinations thereof, or other now known or later developed device for converting to linear attenuation coefficients, segmenting, and reconstructing nuclear data. The processor 22 is a single device or multiple devices operating in serial, parallel, or separately. The processor 22 is specifically designed or provided for reconstruction, but may be a main or general processor of a computer, such as a laptop or desktop computer, or may be a processor for handling tasks in a larger system. The processor 22 may perform other functions than conversion, segmentation and reconstruction.

The processor 22 is configurable. The processor 22 is configured by software and/or hardware. For example, switches, such as dip switches, are set. Potentiometers, resistances, capacitances, inductances, or other devices may be selectable or set. As another example, different software, firmware, and/or instructions are loaded or stored in memory 30 for configuring the processor 22.

The processor 22 is configured to convert signals representing the transmission into linear attenuation coefficients for different locations in the patient. The signals from the CT imaging system 28 are digital or analog and at any stage of processing. For example, the signals are data reconstructed to represent a volume of the patient, but not necessarily in an image or display format. The processor 22 receives the signals and converts the absorption information represented by the signals into a μ-map of linear attenuation coefficients for the volume. The conversion uses two or more functions for different ranges of absorption values. The absorption values themselves are used in a fitting to determine at least one of the functions.

The processor 22 is configured to establish any number of different zones. For example, bone, non-bone, and null zones are established. As another example, at least three tissue zones corresponding to at least three different types of tissues are established. The zones are established using the linear attenuation coefficients. Different locations in the volume are mapped to different zones. Using thresholding, locations with similar or the same linear attenuation coefficients are grouped as a zone. The different zones represent different types of tissue, such as different organs or types of organs.

The processor 22 is configured to iteratively reconstruct an image object representing the patient from the detected emissions and the signals representing the transmission. The signals representing the transmission are used to define the zones, which are used to constrain the reconstruction of the detected emissions. For reconstructing the image object, the zones are separately forward projected. Other processes may be separate by zone, such as renormalization and smoothing. The resulting iterative refinements are combined from the different zones into an updated image object. The signals representing the transmission may additionally be used for attenuation correction as part of the reconstruction.

The memory 30 is a random access memory, graphics processing memory, video random access memory, system memory, cache memory, hard drive, optical media, magnetic media, flash drive, buffer, database, combinations thereof, or other now known or later developed memory device for storing data. The memory 30 stores detected emissions (e.g., PET or SPECT detected event data), signals from transmission (e.g., CT data), zone information, segmentation information, and/or reconstruction information. The memory 30 stores data as processed, such as storing an updated image object or zonal image objects.

The memory 30 or other memory is a non-transitory computer readable storage medium storing data representing instructions executable by the programmed processor 22 for segmentation in multi-modal reconstruction of functional information. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 32 is a monitor, LCD, plasma, touch screen, printer, or other device for displaying an image for viewing by a user. The display 32 shows one or more images representing function, such as uptake. The top row of FIG. 1 shows example images output using multi-modal reconstruction with zones defined by a μ-map converted from absorption measures using multiple functions.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for segmentation in multi-modal reconstruction of functional information, the method comprising:
obtaining computed tomography (CT) data representing a region of a patient;
converting the CT data to linear attenuation coefficients;
segmenting, with the linear attenuation coefficients, locations in the region into at least five types of anatomical tissue, the locations comprising zones segmented between respective types of the anatomical tissue;
generating separate zonal image objects for each of the zones from the functional information;
reconstructing, with a processor, the functional information into an image object, the reconstructing including separately forward projecting the functional information for each zone into data space, wherein a contribution of each zone to a data model is weighted according to a zonal scaling factor for the respective zones; and
generating an image as a function of the image object.

2. The method of claim 1 wherein obtaining the CT data comprises obtaining the CT data in Hounsfield measurement units and wherein converting comprises converting to a μ-map.

3. The method of claim 1 wherein obtaining the CT data comprises obtaining with a CT scanner for a patient using a protocol, and wherein converting the CT data to linear attenuation coefficients comprises adapting to the CT scanner, the patient, and the protocol.

4. The method of claim 1 wherein converting comprises:
comparing a value of the CT data to a predetermined range;
when the value is within a predetermined range, calculating a first linear attenuation coefficient from the value using a first function;
when the value is outside the predetermined range, calculating the first linear attenuation coefficient from the value using a second function different than the first function.

5. The method of claim 4 wherein the predetermined range indicates air-soft tissue and wherein calculating using the first function comprises converting using a linear function calculated from data points of air and water, for which the energy dependence is obtained from a fit to a double-power law, and wherein calculating using the second function comprises converting by a linear fit from soft tissue and bone tissue with a constraint that the second function is continuous over an entire range of Hounsfield units of the CT data.

6. The method of claim 1 wherein segmenting comprises comparing the linear attenuation coefficients for each location with thresholds, the thresholds separating the anatomical tissue by type, the at least five types including dense bone, soft bone, soft tissue, adipose, and lung.

7. The method of claim 1 wherein generating separate zonal image objects comprises separately grouping the functional information for locations into the respective zones.

8. The method of claim 1 further comprising:
smoothing a transition between zones.

9. The method of claim 1 further comprising:
correcting the functional information for attenuation with the linear attenuation coefficients,
wherein segmenting with the linear attenuation coefficients and reconstructing by separately forward projecting the functional information for each zone is in addition to the correcting.

10. The method of claim 1 wherein reconstructing comprises reconstructing the image object from the functional information in combination with the linear attenuation coefficients, the image object having a greater resolution than reconstructing without the combination due to a resolution of the CT data.

11. The method of claim 1 wherein reconstructing comprises reconstructing from a combination of the functional information and the CT data.

12. The method of claim 1 wherein reconstructing comprises combining updated zonal image objects of respective zones of one iteration to form the image object, wherein the contribution of each updated zonal image object to the image object is zone-specific weighted.

13. The method of claim 1 wherein reconstructing comprises:
performing an iterative reconstruction of the image object, wherein the iterative reconstruction comprises a series of iterations, each iteration of which includes forward projecting zonal image objects corresponding to respective zones, thereby generating zonal data models;
combining the zonal data models to form the data model in data space;
determining an update object in object space based on the data model; and
updating the zonal image objects with the update object.

14. The method of claim 1 wherein generating the image comprises rendering the image from the image object.

15. In a non-transitory computer readable storage medium having stored therein data representing instructions executable by a programmed processor for segmentation in multi-modal reconstruction of functional information, the storage medium comprising instructions for:
generating a μ-map from computed tomography (CT) information;
segmenting locations into different zones as a function of the μ-map;
reconstructing from the functional information and the computed tomography information as a multi-modal reconstruction, the reconstructing being based on allocation of different amounts of signal to the different zones according to a contribution in each zone to the functional feature observed.

16. The non-transitory computer readable storage medium of claim 15 wherein generating the μ-map comprises:
comparing a value of the CT information to a predetermined range;
when the value is within the predetermined range, calculating a first linear attenuation coefficient from the value using a linear function based on air and water values;
when the value is outside the predetermined range, calculating the first linear attenuation coefficient from the value using a linear fit from soft tissue and bone tissue with a constraint that the linear fit is continuous over an entire range of Hounsfield units.

17. The non-transitory computer readable storage medium of claim 15 wherein segmenting comprises comparing linear attenuation coefficients for each location with thresholds, the thresholds separating the anatomical tissue by type, at least five types including dense bone, soft bone, soft tissue, adipose, and lung, each zone corresponding to a single one of the types.

18. The non-transitory computer readable storage medium of claim 15 further comprising:
   smoothing a transition between zones.

19. The non-transitory computer readable storage medium of claim 15 wherein reconstructing comprises:
   performing an iterative reconstruction of an image object, wherein the iterative reconstruction comprises a series of iterations, each iteration of which includes forward projecting zonal image objects corresponding to respective zones, thereby generating zonal data models;
   combining the zonal data models to form a data model in data space;
   determining an update object in object space based on the data model;
   updating the zonal image objects with the update object; and
   combining updated zonal image objects of respective zones of one iteration to form the image object, wherein the contribution of each updated zonal image object to the image object is zone-specific weighted; and
   further comprising generating an image of the image object.

20. A multi-modal medical imaging system comprising:
   a computed tomography system configured to detect transmission through a patient;
   a nuclear medicine system configured to detect emissions from the patient;
   a processor configured to convert signals representing the transmission into linear attenuation coefficients for different locations in the patient, configured to establish at least three zones corresponding to at least three different types of tissues, respectively, from the linear attenuation coefficients, and configured to iteratively reconstruct an image object representing the patient from the detected emissions and the signals representing the transmission, the iterative reconstruction including separate forward projecting of the zones.

* * * * *